US007190153B2

(12) United States Patent
Stover et al.

(10) Patent No.: US 7,190,153 B2
(45) Date of Patent: Mar. 13, 2007

(54) SYSTEM, CIRCUIT AND METHOD FOR TUNING A RESONANT CIRCUIT

(75) Inventors: Howard H. Stover, Pasadena, CA (US); Gary L. Heiner, Alhambra, CA (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 95 days.

(21) Appl. No.: 11/123,712

(22) Filed: May 7, 2005

(65) Prior Publication Data

US 2006/0113970 A1    Jun. 1, 2006

Related U.S. Application Data

(60) Provisional application No. 60/632,721, filed on Dec. 1, 2004.

(51) Int. Cl.
*G05F 1/00* (2006.01)
*G05F 1/573* (2006.01)

(52) U.S. Cl. ................ 323/282; 323/284; 323/285
(58) Field of Classification Search ............ 323/282, 323/284, 286
See application file for complete search history.

(56) References Cited

U.S. PATENT DOCUMENTS 5,341,278 A * 8/1994 Brooks ............... 363/16
5,350,413 A    9/1994 Miller
5,917,722 A * 6/1999 Singh ............... 363/132
6,591,139 B2   7/2003 Loftin et al.
6,703,920 B2 * 3/2004 Zimmer ............. 340/10.34
6,889,036 B2 * 5/2005 Ballweber et al. ....... 455/292
7,015,769 B2   3/2006 Schulman et al.
2002/0032471 A1 3/2002 Loftin et al.
2003/0234631 A1 12/2003 Schulman et al.

FOREIGN PATENT DOCUMENTS

WO    WO 98/11942    3/1998

* cited by examiner

*Primary Examiner*—Bao Q. Vu
(74) *Attorney, Agent, or Firm*—Malcolm J. Romano

(57) ABSTRACT

A circuit may be tuned to resonate at a driving frequency. The circuit includes a source that provides an output at a drive frequency and a resonant circuit having an input coupled to the source, an output, and first and second selectable resonant frequencies. The first resonant frequency is below the drive frequency and the second resonant frequency is above the drive frequency. A control coupled to the resonant circuit output selects the first and second resonant frequencies to cause the resonant circuit to provide an output at an apparent resonant frequency equal to the drive frequency.

48 Claims, 4 Drawing Sheets

100

SYSTEM, CIRCUIT AND METHOD FOR TUNING A RESONANT CIRCUIT

CLAIM OF PRIORITY

This application claims priority to U.S. Provisional Application Ser. No. 60/632,721, filed on Dec. 1, 2004, which is incorporated by reference.

BACKGROUND OF THE INVENTION

Implantable medical devices for remedial treatment of and compensation for cardiac, neural and muscular disorders are known in the art. These devices range from cardiac pacemakers as described in U.S. Pat. No. 4,712,555 to Thornander et al., to microstimulators as described in U.S. Pat. No. 6,208,894 to Schulman et al. The quest for minimization of such devices, especially in the area of microdevices such as microstimulators and microsensors continues. Paramount in this quest has been the challenge of efficiently providing a reliable and stable power source to power the device or charge its internal battery. The quest has further addressed the communication medium to facilitate information, data and command signal transfer and exchange between the microdevice and a corresponding microdevice control unit.

Heretofore, wireless communication between the control unit and the implanted device including microdevices, has been described as being implemented by means of a modulated signal, such as a time varying (alternating current AC) magnetic field or light source. In certain instances, wireless communication is also intended as a means of power delivery to an implanted microdevice. This may be achieved by way of a time varying magnetic field generated by an inductor positioned in proximity to the microdevice. The inductor may be formed on a flexible support which contains a series of closely wound electrically conductive wires. When these wires are energized, a magnetic field is generated in the vicinity of the wires.

Such flexible arrangements are useful when it is necessary to bring the inductor in close proximity with microdevices that are implanted in regions of the body characterized as being very contoured. For example, when microdevices are implanted on either side of a patient's neck, the inductor, and therefore the inductor support, must be sufficiently flexible and pliable to permit the inductor to be wrapped around the patient's neck so that the inductor will be in close proximity to the implanted microdevices. With the inductor being so positioned, a maximum magnetic coupling is achieved between the inductor and microdevice. This enables communication, whether it is intended, for example, for data transfer or charging a rechargeable microdevice battery, to be efficiently and reliably realized.

Data transmission between such devices may involve the use of magnetic field modulation techniques using known data transmission protocols. Good wireless communication with magnetic field coupling is best realized when the magnetic field strength is unaffected by manipulation of the inductor support as well as the introduction of magnetic field altering implements in the vicinity of the inductor. Unfortunately, such ideal circumstances are generally not possible and the effective inductance value of the inductor often is caused to change. This can occur, for example, if the inductor is bent or distorted when applied to fit the contour of a desired location of a body.

Magnetic field coupling systems generally use a power source that drives a tuned circuit. The tuned circuit generally comprises an inductor and a capacitor. The maximum power delivered to the tuned circuit, and therefore the maximum magnetic field strength produced by the inductor, occurs when the resonant frequency of the tuned circuit matches a reference frequency, such as a driving frequency.

Most often, the driving frequency of the power source relates to the nominal values of the capacitor and the inductor. Changes in inductance value of the inductor may have a severe impact on the resonant frequency of the tuned circuit. This results in a correspondingly negative effect on the magnetic field generated by the inductor. Deterioration of the magnet c field strength would comprise communication integrity or power transfer between the control unit and the relevant microdevice.

Inductor shape changes from circular to a flattened oval can result in a reduction of inductance value of as much as 50%. Such inductance value changes may be dynamic in nature. Hence, there is a need for a tuning system that dynamically and adaptively adjusts the resonant frequency of the tuned circuit and maintains the resonant frequency substantially equal to the driving frequency. The present invention addresses this and other issues.

SUMMARY

The invention provides a circuit comprising a source that provides an output at a drive frequency and a resonant circuit having an input coupled to the source, an output, and first and second selectable resonant frequencies. The first resonant frequency is below the drive frequency and the second resonant frequency is above the drive frequency. The circuit further comprises a control coupled to the resonant circuit output that selects the first and second resonant frequencies to cause the resonant circuit to provide an output at an apparent resonant frequency equal to the drive frequency.

The resonant circuit may comprise either a series or parallel tuned resonant circuit. The series tuned circuit may comprise an inductor, a first capacitor, and a second capacitor. The second capacitor is selectively switchable in and out of circuit connection with the inductor and first capacitor to provide the selectable first and second resonant frequencies. With a discussion of a series tuned circuit, it is to be appreciated that one skilled in the art may also then configure a system, circuit and method operating with a parallel tuned resonant circuit.

The source may provide a square wave output. Alternatively, the source may provide a sinusoidal output. The control circuit may comprise a switch that selects the first and second resonant frequencies. The switch may comprise a field-effect transistor. The circuit may further comprise a capacitor coupled across the field effect transistor.

The control generates a control signal that operates the switch. The control signal may be a varying duty cycle signal, such as, for example, a pulse-width-modulated signal.

The control signal may have a frequency equal to the drive frequency. Alternatively, the control signal may have a frequency that is different from the drive frequency.

The control may be responsive to current output of the resonant circuit output or phase-shift of the resonant circuit output for selecting the first and second resonant frequencies. Alternatively, the control may be responsive to the voltage output of the resonant circuit output or the output power of the resonant circuit output for selecting the first and second resonant frequencies.

The invention further provides a resonant frequency control circuit comprising a source that provides an output at a drive frequency and a tunable resonant circuit having an input coupled to the source, an output, and a series resonant circuit between the input and output. The series resonant circuit includes an inductance, a first capacitance in series with the inductance and a second capacitance selectably switchable in parallel with the first capacitance. The circuit further comprises a sense circuit coupled to the output of the resonant circuit that senses a characteristic of the resonant circuit, and a control circuit that switches the second capacitance in and out of parallel circuit with the first capacitance responsive to the characteristic of the resonant circuit to cause the resonant circuit to exhibit an apparent resonant frequency equal to the drive frequency.

The invention still further provides a method comprising driving a resonant circuit with a signal at a drive frequency to provide a resonant circuit response and sensing a characteristic of the resonant circuit response. The method further comprises selectively varying, responsive to the sensed characteristic, the resonant frequency of the resonant circuit above and below the drive frequency to provide apparent resonance of the resonant circuit at the drive frequency.

The invention still further provides a system comprising resonant circuit means for providing a variable resonant frequency, means for driving the resonant circuit means with a signal at a drive frequency to cause a resonant circuit means response, and sensing means for sensing a characteristic of the resonant circuit means response. The system further comprises means responsive to the sensed characteristic for selectively varying the resonant frequency of the resonant circuit means above and below the drive frequency for providing apparent resonance of the resonant circuit means at the drive frequency.

BRIEF DESCRIPTION OF THE DRAWINGS

Further features and advantages of the present invention may be more readily understood by reference to the following description taken in conjunction with the accompanying drawings, in which.

DETAILED DESCRIPTION OF THE PREFERRED EMBODIMENTS

This description if not to be taken in a limiting sense, but is made merely for the purpose of describing the general principles of the embodiments of the invention.

Figure 1:
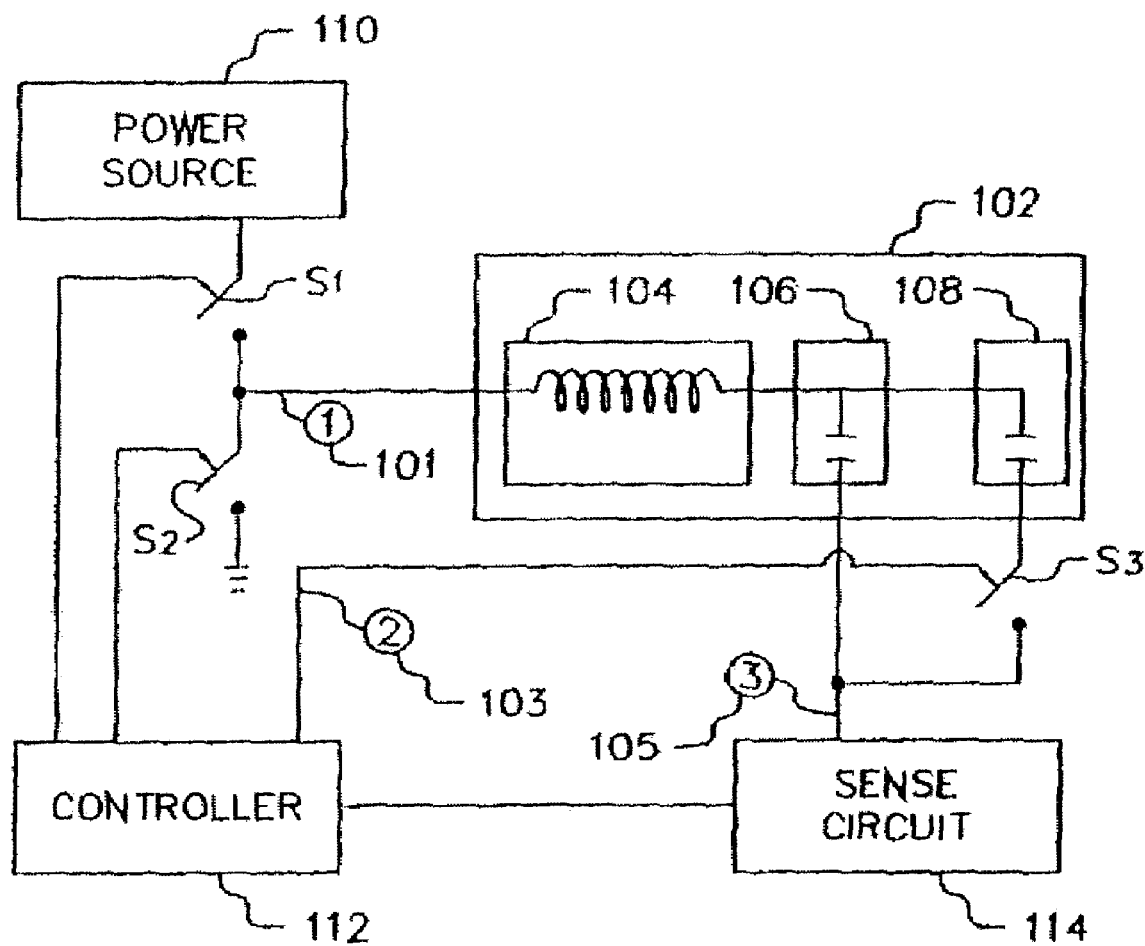
FIG. 1 is a schematic diagram of a tuning system according to one embodiment of the present invention.

FIG. 1 is a schematic diagram of a tuning system or circuit in accordance with a first embodiment of the present invention. The tuning system 100 comprises a tunable resonant circuit 102 comprising an inductor 104, a primary capacitor 106, and a secondary capacitor 108. As will be seen subsequently, the capacitor 108 is switchable in and out of parallel circuit with capacitor 106. The inductor 104 and capacitors 106 and 108 from a series resonant circuit having a first or lower resonant frequency when capacitor 108 is switched in circuit and a second or higher resonant frequency when capacitor 108 is switched out of circuit.

The tuning system 100 further comprises a power source 110. The power source 110 provides power at a first predetermined drive frequency to the tunable resonant circuit 102. To that end, switch S1 and switch S2 alternately couple and de-couple the power source 110 to and from the tunable resonant circuit 102 at the drive frequency.

The circuit 100 further comprises a switch S3. Switch S3 is adapted to switch the secondary capacitor 108 in and out of circuit across the primary capacitor 106. The switch S3 switches responsive to a control signal at a second predetermined frequency, as for example, the drive frequency. The control signal may be a square wave with a controllable duty cycle provided by a controller 112. The controller 112 adjusts the duty cycle of the control signal to cause switch S3 to optimize a parameter or characteristic of the resonant circuit response. The parameter or characteristic may be sensed by a sense circuit 114. The sensed parameter or characteristic may be any one or combination of a number of parameters, as, for example, current, phase-shift, voltage, or power.

The tunable resonant circuit 102 has two natural resonant frequencies. The first natural resonant frequency is below the drive frequency and results from the circuit including the inductance of the inductor 104 and the total capacitance of the primary capacitor 106 and the switched in circuit secondary capacitor 108. The second natural resonant frequency is above the drive frequency and results from the inductance of the inductor 104 and the primary capacitor 106. Here, the capacitor 108 is switched out of circuit.

As shown in FIG. 1, the sense circuit 114 is coupled to the tunable resonant circuit 102 to monitor and measure the values of the resonant circuit response parameter or characteristic in order to determine the amount of energy transfer from the power source 110 to the inductor 104. The aim is for the energy transfer to be a maximum, obtainable by maintaining the resonant circuit 102 at resonance with the drive frequency. In this regard, the aim is to have the current delivered to the resonant circuit in phase with the voltage across the resonant circuit.

The first natural resonant frequency is below the drive frequency substantially at the low end of a range of resonant frequencies that may be produced by the combination of the inductor 104, primary capacitor 106 and the secondary capacitor 108. The second natural resonant frequency, however, is above the drive frequency substantially at the high end of the range of resonant frequencies that may be produced by the combination of the inductor 104 and the primary capacitor 106 with capacitor 108 switched out of circuit.

By switching the switch S3 to a closed position the secondary capacitor 108 is added to the tunable circuit 102 by being placed in parallel with the primary capacitor 106. Therefore, the tunable circuit 102 is tuned to the first natural resonant frequency below the drive frequency for the length of time that switch S3 is closed. Conversely, when the switch S3 is open, the secondary capacitor 108 is out of circuit and not part of the tuned circuit 102. The tunable circuit 102 is then tuned to the second natural resonant frequency above the drive frequency for the length of time that switch S3 is open.

According to this embodiment of the present invention, the switch S3 is operated based on a varying duty cycle control signal from controller 112, such as a pulse-width-modulated (PWM) signal. Its duty cycle is such that switch S3 is closed for a length of time and open for another length of time depending on the value of the sensed resonant circuit response characteristic. Therefore, a waveform resulting (resultant waveform) from the above switching protocol has the characteristics of both the waveform associated with first natural resonant frequency and the waveform associated with the second natural resonant frequency in varying proportion depending on the length of time that switch S3 is closed or open, i.e., duty cycle.

Figure 2:
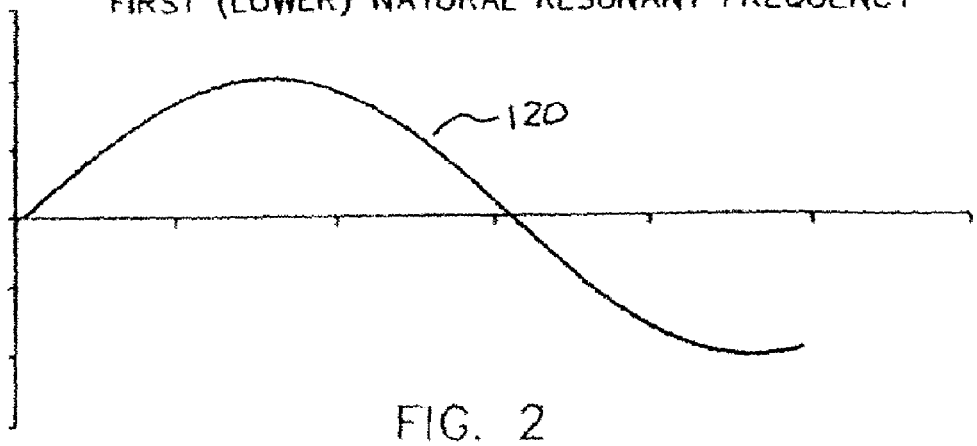
FIG. 2 is an illustration of a waveform associated with a first natural resonant frequency of a tunable circuit according to an embodiment of the present invention.
Figure 3:
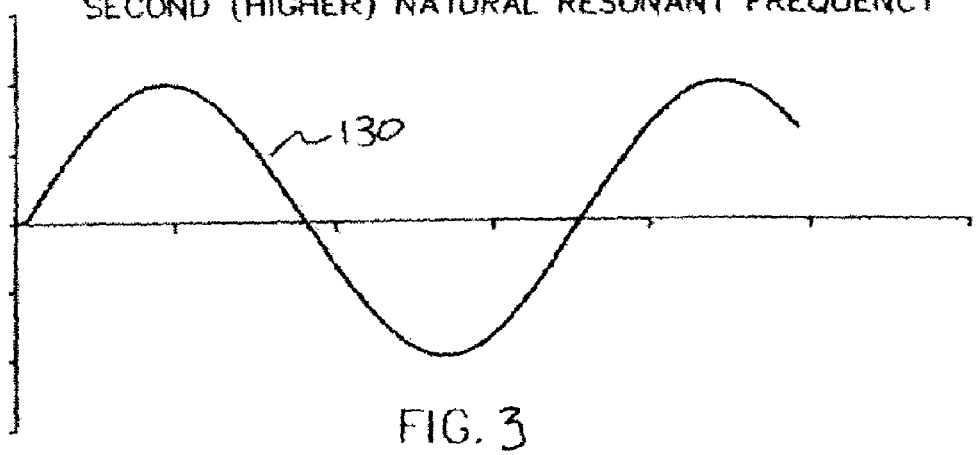
FIG. 3 is an illustration of another waveform associated with a second natural resonant frequency of a tunable circuit according to an embodiment of the present invention.
Figure 4:
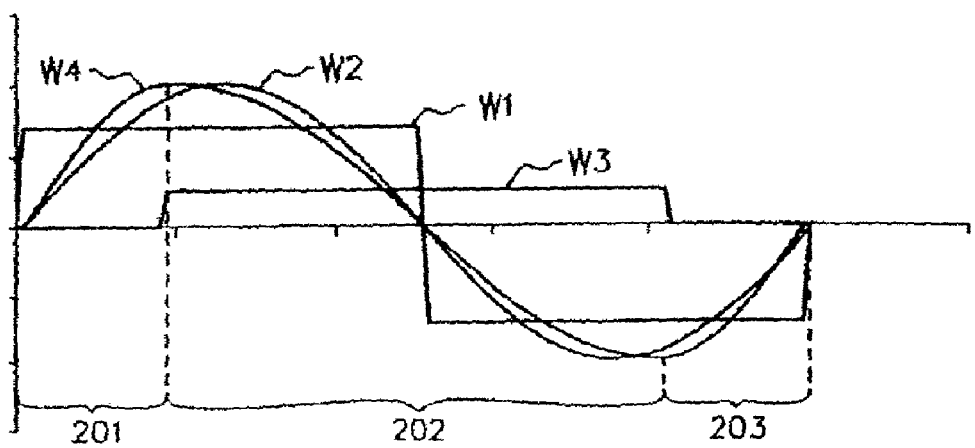
FIG. 4 is an illustration of a resultant waveform which comprises segments of waveforms in FIG. 2 and FIG. 3 and other waveforms according to an embodiment of the present invention.

FIG. 2 is an illustration of a waveform 120 associated with the first or lower frequency natural resonant frequency of the tunable circuit according to this embodiment of the present invention. FIG. 3 is an illustration of another waveform 130 associated with the second or higher frequency natural resonant frequency of the tunable circuit according to this embodiment of the present invention. FIG. 4 is an illustration of the resultant waveform which comprises component segments of both of the waveforms of the first and second resonant frequencies.

Referring to FIG. 4, it shows an exemplary single cycle of the driving waveform W1 of source 110 provided at the driving frequency. It is a square-wave resulting from the switching of switches S1 and S2 of FIG. 1.

Also shown in FIG. 4 is waveform W2 which is a representation of an ideal response of a resonant circuit tuned substantially to the driving frequency. Again, referring to FIG. 4, a waveform W3 is also shown which illustrates a control waveform from controller 112 having substantially the same frequency as the driving frequency and with a predetermined duty cycle which determines the ON time (when W3 is high) and OFF time (when W3 is low) of switch S3. It should be noted that waveform W3 is an example of a PWM signal driving switch S3.

With further reference to FIG. 4, the resultant waveform W4 is shown that comprises the two waveforms associated with the first natural resonant frequency and the second natural resonant frequency. By way of example, when the square wave W3 is low, the switch S3 is open. Hence, the tunable resonant circuit 102 operates at the second or higher natural frequency. This corresponds to a first portion 201 of the resultant waveform W4 which has the waveform associated with the second or higher natural resonant frequency. When W3 is high, the switch S3 is closed. Hence, the tunable resonant circuit 102 operates at the first or lower natural frequency. As a result, a second portion 202 of the resultant waveform which has W4 the waveform associated with the first or lower natural resonant frequency. Finally, when the control signal W3 is low again for the rest of the cycle, the third portion 203 of the resultant waveform W4 again corresponds to the waveform associated with the second or higher natural resonant frequency. The test points 1, 2, and 3 marked as encircled numerals and indicated at locations 101, 103, and 105 respectively in FIG. 1 correspond to the waveforms shown in FIG. 4. Specifically, driving waveform W1 in FIG. 4, corresponds to test point 1, indicated at 101 in FIG. 1; control signal waveform W3 in FIG. 4, corresponds to test point 2, indicated at 103 in FIG. 1; and resultant waveform W4 in FIG. 4, corresponds to test point 3, indicated at 105 in FIG. 1. As will be appreciated by those skilled in the art, these waveforms are exemplary of the functioning of the tuning system in the embodiments of the present invention.

It should be noted that in the present embodiments, the resultant waveform corresponds to a net response resulting from the switching between the first and second natural resonant frequency in such proportion that the net response simulates resonance at the driving frequency. The ideal response, namely waveform W2, of a resonant circuit tuned substantially to the driving frequency is thereby emulated. Hence, varying the pulse width of the control signal W3 (the duty cycle) can cause the net response to substantially simulate the response of a resonant circuit tuned to any frequency in the range between the first natural resonant frequency below the driving frequency and the second natural resonant frequency above the driving frequency.

If the inductance of the inductor 104 changes because of physical distortions, temperature changes or any other causes, then the resonant frequency of the tuning system 100 will change accordingly. The sense circuit 114 measures the changes in the parameters of the system and therefore, generates and provides a signal to the controller 112 indicative of the change in the value of a particular parameter. For example, the parameter measured may be the value of the resonant circuit current amplitude in the system. If it drops below a desired or a predetermined value, it will indicate that the response of the tunable circuit 102 is not optimal, i.e., it does not simulate the response of a resonant circuit that is tuned substantially to the driving frequency. The parameter measured may alternatively or in addition by the phase-shift in the current waveform. This also can be an indicator that the tunable circuit 102 is not operating optimally. As described above, other electrical parameters of the system which may be monitored include power, voltage or other parameters indicative of the operation of the tunable circuit 102. As will be appreciated by those skilled in the art, in order to optimize the tunable circuit 102, the electrical parameters should be optimized such that the current amplitude, voltage and power are maximized, whereas the phase-shift is minimized.

According to this embodiment, the controller 112 receives the signal indicative of an electrical parameter from the sense circuit 114 and, based on the value of the signal received, adjusts the duty cycle of switch S3 by providing a pulse-width-modulated signal to the switch S3. By closing and opening switch S3 at varying times during a driving cycle, the secondary capacitor 108 is placed in parallel circuit with the primary capacitor 106 or removed out of circuit from the tunable circuit 102. This provides an optimized waveform that simulates a desired apparent resonant response of the tuned circuit to the driving frequency for optimized magnetic field generation and power transfer by the inductor 104.

According to an alternate embodiment of the present invention, the second predetermined frequency associated with the operation of switch S3 may be different from the driving frequency associated with the operation of switch S1 and switch S2. In such instance, the duty cycle of switch S3 may span over more than one driving cycle or it may be shorter than one driving cycle.

Figure 5:
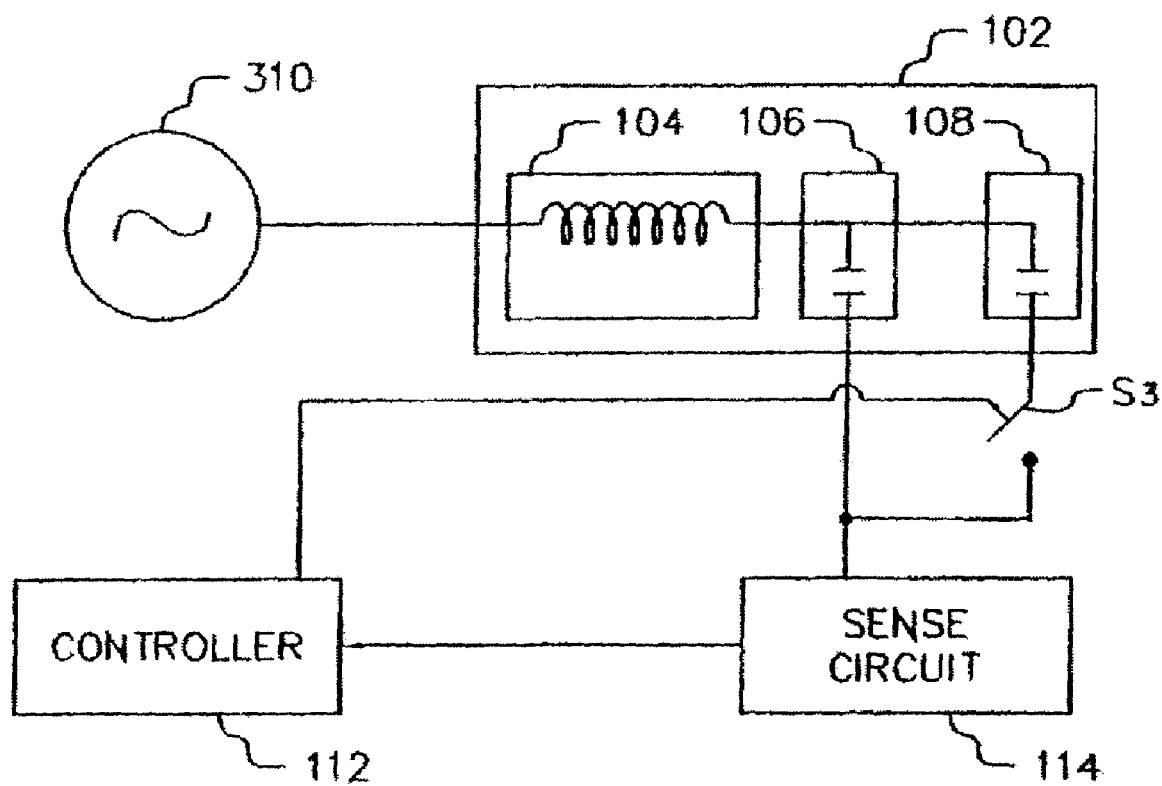
FIG. 5 is a schematic diagram of a tuning system according to an alternative embodiment of the present invention wherein a sinusoidal source is utilized as a power source.

In a further alternative embodiment of the present invention, the power source may provide a sinusoidal signal instead of a square wave. Hence, the operation of the tunable circuit 102 is not limited to a particular power source. Referring to FIG. 5, it shows a sinusoidal power source 310. The sinusoidal power source 310 is coupled to the tunable circuit 102. In this embodiment, the switch S1 and switch S2 are removed from the tuning system 100 and the controller 112 controls the operation of switch S3 as described in connection with the embodiments described above.

Figure 6:
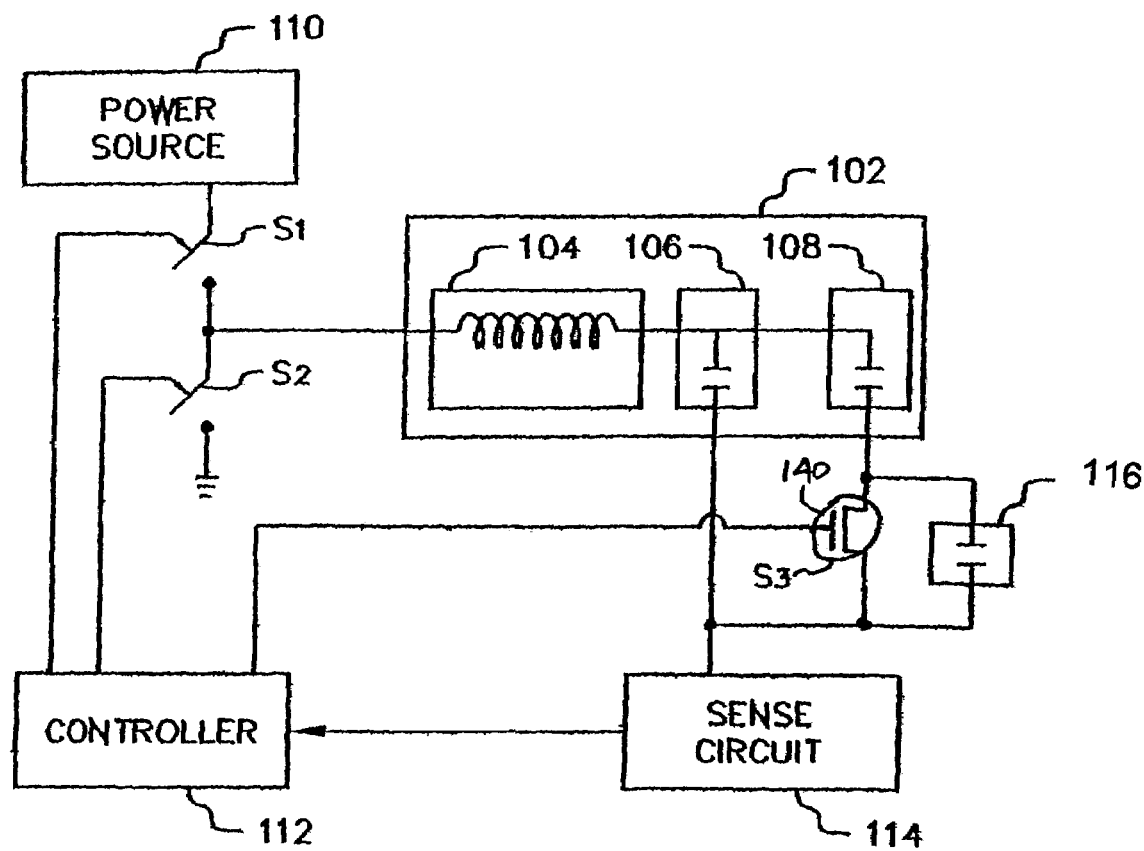
FIG. 6 is a schematic diagram of yet a further tuning system according to a further embodiment of the present invention.

In yet a further alternative embodiment of the present invention, a third capacitor may be provided and placed in parallel with the switch S3 of the embodiments shown in FIGS. 1 and 5. Referring to FIG. 6, the third capacitor 116 is shown placed in parallel with the switch S3. When switch S3 is in a form of a field-effect transistor (FET) 140, there may be voltage spikes generated during the switching of the FET. Therefore, the third capacitor 116 reduces the voltage spikes during the opening and closing of the FET. It also reduces the peak voltage across the FET. Additionally, the third capacitor 116 mitigates the voltage dependent output capacitance of the FET used for switch S3, thereby providing better linearity in the tunable circuit.

The descriptions of the invention, the specific details, and the drawings mentioned above, are not meant to limit the scope of the present invention. The present invention may be embodied in other specific forms without departing from its spirit or essential characteristics. The described embodiments are to be considered in all respects only as illustrative and not restrictive. All changes, which come within the meaning and range of equivalency of the claims, are to be embraced within their scope.

What is claimed is:

1. A circuit comprising:
   a source that provides an output at a drive frequency;
   a resonant circuit having an input coupled to the source, an output, and first and second selectable resonant frequencies, the first resonant frequency being below the drive frequency and the second resonant frequency being above the drive frequency; and
   a control coupled to the resonant circuit output that selects the first and second resonant frequencies to cause the resonant circuit to provide an output at an apparent resonant frequency equal to the drive frequency.

2. The circuit of claim 1 wherein the resonant circuit comprises a series tuned resonant circuit.

3. The circuit of claim 1 wherein the resonant circuit comprises an inductor, a first capacitor, and a second capacitor, the second capacitor being selectively switchable in and out of circuit with the inductor and first capacitor to provide the selectable first and second resonant frequencies.

4. The circuit of claim 3 wherein the inductor and first capacitor are coupled in series and wherein the second capacitor is switchable in parallel with the first capacitor.

5. The circuit of claim 1 wherein the source provides a square wave output.

6. The circuit of claim 1 wherein the source provides a sinusoidal output.

7. The circuit of claim 1 wherein the control comprises a switch that selects the first and second resonant frequencies.

8. The circuit of claim 7 wherein the switch comprises a field effect transistor.

9. The circuit of claim 8 further comprising a capacitor coupled across the field effect transistor.

10. The circuit of claim 7 wherein the control generates a control signal that operates the switch.

11. The circuit of claim 10 wherein the control signal is a varying duty cycle signal.

12. The circuit of claim 11 wherein the varying duty cycle signal is a pulse-width-modulated signal.

13. The circuit of claim 10 wherein the control signal has a frequency equal to the drive frequency.

14. The circuit of claim 10 wherein the control signal has a frequency that is different than the drive frequency.

15. The circuit of claim 1 wherein the control is responsive to current output of the resonant circuit output for selecting the first and second resonant frequencies.

16. The circuit of claim 1 wherein the control is responsive to phase-shift of the resonant circuit output for selecting the first and second resonant frequencies.

17. The circuit of claim 1 wherein the control is responsive to voltage output of the resonant circuit output for selecting the first and second resonant frequencies.

18. The circuit of claim 1 wherein the control is responsive to output power of the resonant circuit output for selecting the first and second resonant frequencies.

19. A resonant frequency control circuit comprising:
    a source that provides an output at a drive frequency;
    a tunable resonant circuit having an input coupled to the source, an output, and a series resonant circuit between the input and output, the series resonant circuit including an inductance, a first capacitance in series with the inductance and a second capacitance selectably switchable in parallel with the first capacitance;
    a sense circuit coupled to the output of the resonant circuit that senses a characteristic of the resonant circuit; and
    a control circuit that switches the second capacitance in and out of parallel circuit with the first capacitance responsive to the characteristic of the resonant circuit to cause the resonant circuit to exhibit an apparent resonant frequency equal to the drive frequency.

20. The circuit of claim 19 wherein the resonant circuit has a first resonant frequency below the drive frequency when the second capacitance is in parallel circuit with the first capacitance and a second resonant frequency above the drive frequency when the second capacitance is out of parallel circuit with the first capacitance.

21. The circuit of claim 19 wherein the source provides a square wave output.

22. The circuit of claim 19 wherein the source provides a sinusoidal output.

23. The circuit of claim 20 wherein the control circuit includes a switch that switches the second capacitance in and out of parallel circuit with the first capacitance.

24. The circuit of claim 23 wherein the switch comprises a field effect transistor.

25. The circuit of claim 24 further comprising a capacitor coupled across the field effect transistor.

26. The circuit of claim 23 wherein the control circuit generates a control signal that operates the switch.

27. The circuit of claim 26 wherein the control signal is a varying duty cycle signal.

28. The circuit of claim 27 wherein the varying duty cycle signal is a pulse-width-modulated signal.

29. The circuit of claim 26 wherein the control signal has a frequency equal to the drive frequency.

30. The circuit of claim 26 wherein the control signal has a frequency that is different than the drive signal.

31. The circuit of claim 19 wherein the characteristic is current output.

32. The circuit of claim 19 wherein the characteristic is phase-shift.

33. The circuit of claim 19 wherein the characteristic is voltage output.

34. The circuit of claim 19 wherein the characteristic is output power.

35. A method comprising:
    driving a resonant circuit with a signal at a drive frequency to provide a resonant circuit response;
    sensing a characteristic of the resonant circuit response; and responsive to the characteristic, selectively varying the resonant frequency of the resonant circuit above and below the drive frequency to provide apparent resonance of the resonant circuit at the drive frequency.

36. The method of claim 35 wherein the resonant circuit comprises an inductor, a first capacitor, and a second capacitor, and wherein the varying step includes selectively switching the second capacitor in and out of circuit with the inductor and the first capacitor.

37. The method of claim 36 wherein the inductor and first capacitor are coupled in series and wherein the varying step further includes switching the second capacitor in and out of parallel circuit with the first capacitor.

38. The method of claim 35 wherein the driving step includes providing a square wave signal.

39. The method of claim 35 wherein the driving step includes providing a sinusoidal signal.

40. The method of claim 35 wherein the varying step includes generating a varying duty cycle signal.

41. The method of claim 40 wherein the varying duty cycle signal is a pulse-width-modulated signal.

42. The method of claim 40 wherein the varying duty cycle signal has a frequency equal to the drive frequency.

43. The method of claim 40 wherein the varying duty cycle signal has a frequency that is different than the drive frequency.

44. The method of claim 35 wherein the characteristic is current output.

45. The method of claim 35 wherein the characteristic is phase-shift.

46. The method of claim 35 wherein the characteristic is voltage output.

47. The method of claim 35 wherein the characteristic is output power.

48. A system comprising:

resonant circuit means for providing a variable resonant frequency;

means for driving the resonant circuit means with a signal at a drive frequency to cause a resonant circuit means response;

sensing means for sensing a characteristic of the resonant circuit means response; and means responsive to the characteristic for selectively varying the resonant frequency of the resonant circuit means above and below the drive frequency for providing apparent resonance of the resonant circuit means at the drive frequency.

* * * * *